(12) United States Patent
Katsuhara et al.

(10) Patent No.: US 8,865,946 B2
(45) Date of Patent: Oct. 21, 2014

(54) PROCESS FOR PRODUCING FLUOROMETHYL HEXAFLUOROISOPROPYL ETHER

(75) Inventors: Yutaka Katsuhara, Kawagoe (JP); Hiroshi Takahashi, Osato-gun (JP); Michio Ishida, Noda (JP)

(73) Assignee: Central Glass Company, Limited, Ube-shi (JP)

( * ) Notice: Subject to any disclaimer, the term of this patent is extended or adjusted under 35 U.S.C. 154(b) by 310 days.

(21) Appl. No.: 13/258,195

(22) PCT Filed: Apr. 9, 2010

(86) PCT No.: PCT/JP2010/056458
§ 371 (c)(1),
(2), (4) Date: Sep. 21, 2011

(87) PCT Pub. No.: WO2010/125899
PCT Pub. Date: Nov. 4, 2010

(65) Prior Publication Data
US 2012/0041237 A1    Feb. 16, 2012

(30) Foreign Application Priority Data
Apr. 28, 2009   (JP) .................................. 2009-109033

(51) Int. Cl.
*C07C 41/14*    (2006.01)

(52) U.S. Cl.
CPC ...................................... *C07C 41/14* (2013.01)
USPC ........................................................ 568/683

(58) Field of Classification Search
CPC .............................. C07C 43/123; C07C 41/22
USPC ........................................................ 568/683
See application file for complete search history.

(56) References Cited

U.S. PATENT DOCUMENTS

| 4,250,334 | A | 2/1981 | Coon et al. |
| 5,990,359 | A | 11/1999 | Ryan et al. |
| 6,469,219 | B1 | 10/2002 | Khrimian et al. |
| 6,987,204 | B2 | 1/2006 | Rozov et al. |
| 7,034,190 | B2 | 4/2006 | Sharratt et al. |
| 7,153,397 | B2 | 12/2006 | Sharratt et al. |
| 7,375,254 | B2 | 5/2008 | Rozov et al. |

FOREIGN PATENT DOCUMENTS

| JP | 59-204142 | A | 11/1984 |
| JP | 1-301631 | A | 12/1989 |
| JP | 7-502037 | A | 3/1995 |
| JP | 2000-503021 | A | 3/2000 |
| JP | 2004-520308 | A | 7/2004 |
| JP | 2004-520310 | A | 7/2004 |
| JP | 2006-516282 | A | 6/2006 |
| WO | WO 93/12057 | A1 | 6/1993 |
| WO | WO 93/22265 | * | 11/1993 .............. C07C 41/01 |
| WO | WO 97/25303 | A1 | 7/1997 |
| WO | WO 02/50003 | A1 | 6/2002 |

OTHER PUBLICATIONS

European Search Report dated Nov. 26, 2012 (five (5) pages).
Corresponding International Search Report with English Translation dated Jun. 15, 2010 (five (5) pages).
Form PCT/ISA/237 ( three (3) pages).
Chinese Office Action dated Aug. 19, 2013 {Five (5) pages}.
Duanshou, Xie et al., "Physical Property Data of Common Matters", Chemical Technology Nomograph, 1982, pp. 445-446, vol. 1, Chemical Industry Press.

* cited by examiner

*Primary Examiner* — Rosalynd Keys
(74) *Attorney, Agent, or Firm* — Crowell & Moring LLP

(57) ABSTRACT

There is provided according to the present invention a process for producing fluoromethyl hexafluoroisopropyl ether $((CF_3)_2CH-O-CH_2F)$, including: reacting bisfluoromethyl ether with hexafluoroisopropyl alcohol in a solvent substantially immiscible with hydrogen fluoride in the presence of a catalytic amount of a strong acid selected from sulfuric acid and any other acids stronger in acidity than sulfuric acid. The process of the present invention enables industrial production of the fluoromethyl hexafluoroisopropyl ether without using hydrogen fluoride or a large amount of sulfuric acid and thereby without causing a large amount of waste as a by-product.

3 Claims, No Drawings

PROCESS FOR PRODUCING FLUOROMETHYL HEXAFLUOROISOPROPYL ETHER

TECHNICAL FIELD

The present invention relates to a process for producing fluoromethyl hexafluoroisopropyl ether, which is used as an inhalation anesthetic.

BACKGROUND ART

Fluoromethyl hexafluoroisopropyl ether, known as "Sevoflurane", is used as an inhalation anesthetic with good anesthetic performance. As a production method of fluoromethyl hexafluoroisopropyl ether, there is known a process of reacting formaldehyde (paraformaldehyde) with hexafluoroisopropyl alcohol in a liquid phase by the use of sulfuric acid as a dehydrating agent in hydrogen fluoride (see Patent Document 1). Further, there is proposed a process for obtaining fluoromethyl hexafluoroisopropyl ether by selective solvent extraction or distillation, in place of using a dehydrating agent, from a reaction mixture in which hexafluoroisopropyl alcohol and formaldehyde are in equilibrium in hydrogen fluoride (see Patent Document 2). It has been found that several percentages of fluoromethyl hexafluoroisopropyl ether can be obtained by mixing hydrogen fluoride with formaldehyde (trioxane), cooling the mixture, adding hexafluoroisopropanol to the mixture, and then, stirring the resulting mixture (see Patent Document 3). There is also proposed a process for producing fluoromethyl hexafluoroisopropyl ether by reacting high-purity bisfluoromethyl ether with hexafluoroisopropyl alcohol in the presence of sulfuric acid (see Patent Documents 4 and 5).

PRIOR ART DOCUMENTS

Patent Documents

Patent Document 1: U.S. Pat. No. 4,250,334
Patent Document 2: U.S. Pat. No. 6,469,219
Patent Document 3: Japanese Laid-Open Patent Publication No. H07-502037
Patent Document 4: International Publication No. WO 97/25303
Patent Document 5: Japanese Laid-Open Patent Publication No. 2004-520308

SUMMARY OF THE INVENTION

Problems to be Solved by the Invention

The production process of Patent Document 1 has difficulty in wasting the sulfuric acid used as the dehydrating agent. The production process of Patent Document 2 uses a large amount of hydrogen fluoride to e.g. separate Sevoflurane from the reaction system by azeoptropic extraction with hydrogen fluoride and requires extra caution in handling such a large amount of hydrogen fluoride. The process of Patent Document 3 is low in yield and is not so practical. The production process of Patent Document 4 has the possibility of generating a large amount of liquid waste containing sulfuric acid or hydrofluoric acid due to the use of 1 mL of 98% sulfuric acid per 2 g of bisfluoromethyl ether and 4.1 g of hexafluoroisopropyl alcohol. The production process of Patent Document 5, which is similar to the production process of Patent Document 4, also has the possibility of generating a large amount of liquid waste containing sulfuric acid or hydrofluoric acid due to the use of 20 mL of sulfuric acid per 100 μL of bisfluoromethyl ether and about 16 μL of hexafluoroisopropyl alcohol. There is technical difficulty in recovering sulfuric acid and hydrogen fluoride or hydrofluoric acid from the liquid waste. It is thus common practice to fix the waste acid with a basic substance and dispose of the fixed acid waste. However, the disposal of such waste acid raises a concern of environmental load.

It is therefore an object of the present invention to provide an industrially applicable process for producing fluoromethyl hexafluoroisopropyl ether (($CF_3$)$_2$CH—O—$CH_2$F) without using hydrogen fluoride or a large amount of sulfuric acid and thereby without causing a large amount of waste acid as a by-product.

Means for Solving the Problems

In order to solve the above problems, the present inventors have made researches on the production of fluoromethyl hexafluoroisopropyl ether with the use of bisfluoromethyl ether and hexafluoroisopropyl alcohol as raw materials but without the use of hydrogen fluoride and have found that, in the case of reacting bisfluoromethyl ether and hexafluoroisopropyl alcohol in the presence of an acid catalyst, it is possible by the coexistence of a specific solvent in the reaction system to reduce the amount of the acid catalyst to a significantly small level and allow the reaction to proceed even under moderate conditions.

Namely, the present invention includes the following features.

[Inventive Feature 1]

A process for producing fluoromethyl hexafluoroisopropyl ether, comprising: reacting bisfluoromethyl ether with hexafluoroisopropyl alcohol in a solvent substantially immiscible with hydrogen fluoride in the presence of a catalytic amount of a strong acid selected from sulfuric acid and any other acids stronger in acidity than sulfuric acid.

[Inventive Feature 2]

The process for producing fluoromethyl hexafluoroisopropyl ether according to Inventive Feature 1, wherein the solvent is any of halogenated aliphatic hydrocarbons and halogenated aromatic hydrocarbons.

[Inventive Feature 3]

The process for producing fluoromethyl hexafluoroisopropyl ether according to Inventive Feature 1 or 2, wherein the strong acid is one kind, or two or more kinds, selected from the group consisting of sulfuric acid, trifluoromethanesulfonic acid and fluorosulfuric acid.

The process of the present invention enables industrial production of fluoromethyl hexafluoroisopropyl ether (($CF_3$)$_2$CH—O—$CH_2$F) without using hydrogen fluoride or a large amount of sulfuric acid and thereby without causing a large amount of waste catalyst as a by-product.

BEST MODES FOR CARRYING OUT THE INVENTION

Hereinafter, the present invention will be described in detail below. In the present specification, bisfluoromethyl ether, hexafluoroisopropyl alcohol and fluoromethyl hexafluoroisopropyl ether may sometimes be abbreviated as "FE", "HFIP" and "SEVO", respectively.

In the present invention, fluoromethyl hexafluoroisopropyl ether is produced by reaction of bisfluoromethyl ether and hexafluoroisopropyl alcohol in a specific solvent in the presence of a catalytic amount of a strong acid selected from sulfuric acid and any other acids stronger in acidity than sulfuric acid.

Namely, the bisfluoromethyl ether $(CH_2)_2F$—O—$CH_2F)$ is reacted with the hexafluoroisopropyl alcohol $((CF_3)_2CHOH)$ by the catalytic action of the strong acid in the production process of the fluoromethyl hexafluoroisopropyl ether according to the present invention. The following equilibrium is established in the reaction system.

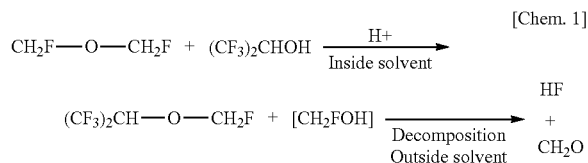

Fluoromethanol ($CH_2FOH$) generated as a by-product is unstable and immediately decomposed into hydrogen fluoride and formaldehyde ($CH_2O$) under the equilibrium. It is assumed that, due to the facts that: hydrogen fluoride is substantially insoluble in the solvent of the present invention; and fluoromethyl hexafluoroisopropyl ether is soluble in the solvent of the present invention, the existence of the solvent of the present invention in the present equilibrium system makes it possible that the fluoromethyl hexafluoroisopropyl ether can be obtained efficiently by letting out the hydrogen fluoride from the solvent but allowing the fluoromethyl hexafluoroisopropyl ether to remain in the solvent.

In the present invention, the hexafluoroisopropyl alcohol is used in an amount of 0.1 to 1000 parts by mass per 100 parts by mass of the bisfluoromethyl ether. It is preferable to use 0.5 to 500 parts by mass of the hexafluoroisopropyl alcohol per 100 parts by mass of the bisfluoromethyl ether. As is apparent from the above reaction formula, the reaction of the bisfluoromethyl ether with the hexafluoroisopropyl alcohol is a 1:1 reaction. Although it is suffice to use the hexafluoroisopropyl alcohol and the bisfluoromethyl ether at a molar ratio of 1:1, either one of the hexafluoroisopropyl alcohol and the bisfluoromethyl ether may be used in a larger amount than that of the other in view of the availability of these raw materials.

There is no particular limitation on the method of preparation of the FE and HFIP as the raw materials in the present invention. The raw materials can be prepared by any known methods. For example, it is feasible to prepare the FE by reaction of formaldehyde and hydrogen fluoride as disclosed in Patent Document 3 and is feasible to prepare the HFIP by catalytic reduction of hexafluoroacetone hydrate in a liquid phase as disclosed in Japanese Laid-Open Patent Publication No. S59-204142 and in Japanese Laid-Open Patent Publication No. H01-301631.

In the present invention, the strong acid used as a catalyst is selected from sulfuric acid and any other acids stronger in acidity (larger in acid dissociation constant) than sulfuric acid. Specific examples of such a strong acid are: sulfuric acid (Hammett acidity function Ho=−12, pKa=−5.0); trifluoromethanesulfonic acid (Ho=−14.9, pKa=−13); fluorosulfuric acid (Ho=−15); imidic acid $[(CF_3SO_2)_2NH]$; and methide acid $[(CF_3SO_2)_3CH]$. Among others, sulfuric acid, trifluoromethanesulfonic acid and fluorosulfuric acid are particularly preferred as these acids are readily available. The strong acid is used in a sufficient amount to allow the reaction to proceed (referred to as "catalytic amount" in the present specification). The amount of the acid used as the catalyst is 0.0001 to 10 parts by mass, preferably 0.001 to 1 part by mass, per 100 parts by mass of the reaction solution constituting the reaction system. In practice, the acid amount is not limitative and can be set automatically within the range that the acid can be dissolved in the solvent used. If the amount of the acid falls within the above range but exceeds the solubility limit, the reaction solution cannot be obtained as a uniform solution by the addition of the acid so that it is useless to add such an excessive amount of acid. The rate of the reaction is unfavorably low if the amount of the acid is smaller than the above range. It is feasible to dissolve a catalytic amount of strong acid in the solvent by adding the strong acid to the solvent, stirring the acid and the solvent well, and then, isolating the undissolved acid from the solvent. The strong acid such as sulfuric acid can be used in the form of a commercially available reagent or an industrial material as it is.

The solvent of the present invention is required to dissolve therein the catalytic amount of strong acid and the bisfluoromethyl ether, be stable in the presence of the strong acid and be substantially immiscible with hydrogen fluoride. It means that, when the solvent is substantially immiscible with hydrogen fluoride, the hydrogen fluoride is substantially insoluble, almost insoluble or at least not completely soluble in the solvent. As such a solvent, there can be used any of halogenated aliphatic hydrocarbons and halogenated aromatic hydrocarbons. Specific examples of the halogenated aliphatic hydrocarbons are dichloromethane, chloroform, tetrachloromethane, dichloroethane, trichloroethane, tetrachloroethane, trichlorotrifluoroethane, 1,1,1,3,3-pentafluoropropane (HFC-245fa) and 1-chloro-3,3,3-trifluoropropene (HCFC-1233). Specific examples of the halogenated aromatic hydrocarbons are benzotrifluoride, bistrifluoromethylbenzene and 2,4-dichlorobenzotrifluoride. As these solvents can dissolve therein a slight amount of strong acid such as sulfuric acid or trifluoromethanesulfonic acid, are stable in the presence of the strong acid, and can dissolve therein the FE, it is possible to carry out the reaction of the FE with the HFIP under moderate conditions and thereby produce the SEVO by the use of any of these solvents. Further, these solvents may be used in combination of two or more kinds thereof. There is no particular limitation on the amount of the solvent in the reaction system. The solvent is generally used in an amount of 0.1 to 99.9 parts by mass per 100 parts by mass of the total amount of the reaction system. It is preferable to use 1 to 99 parts by mass, more preferably 5 to 95 parts by mass, of the solvent per 100 parts by mass of the total amount of the reaction system. If the amount of the solvent is less than 0.1 part by mass, the solvent unfavorably does not perform its function. If the amount of the solvent exceeds 99.9 parts by mass, the proportion of the reaction substrates in the reaction system is so low that the productivity of the reaction system is unfavorably decreased.

In the present invention, the reaction temperature is in the range of 0 to 150° C., preferably 5 to 100° C., more preferably 30 to 80° C. If the reaction temperature is lower than 0° C., the rate of the reaction is low. If the reaction temperature exceeds 150° C., it is necessary to use a special pressure-resistance reaction container and externally pressurize the container with nitrogen or the like in order to carry out the reaction in a liquid phase. Under such pressurized conditions, however, the amount of impurities in the reaction product is unfavorably increased even though the rate of the reaction is made high.

The reaction time is in the range of 1 minute to 100 hours, generally 10 minutes to 50 hours, and can be set as appropriate in the present invention. Although the reaction can be performed in either a batch system or a flow system, it is preferable to perform the reaction in a batch system. Further, the reaction can be performed with or without stirring.

Not only the fluoromethyl hexafluoroisopropyl ether but also the unreacted bisfluoromethyl ether, hydrogen fluoride etc. are contained in the reaction product of the present invention. There is no particular limitation on the method of extraction of the fluoromethyl hexafluoroisopropyl ether from the reaction product. The fluoromethyl hexafluoroisopropyl ether can be extracted from the reaction product by any known method. For example, it is feasible to extract the fluoromethyl hexafluoroisopropyl ether by placing the reaction product in water to thereby separate the reaction product into an aqueous layer containing an acid component and a solvent layer, and then, distillating the solvent layer. In order to separate the acid component by water washing as mentioned above, it is desirable to use the solvent insoluble or difficult to dissolve in water.

EXAMPLES

The present invention will be described in more detail below by way of the following examples. It should be noted that these examples are illustrative and are not intended to limit the present invention thereto. In the following examples, the analysis of organic substances was conducted by gas chromatography (with a FID detector) unless otherwise specified.

Example 1

In a 20-mL lidded glass container, 5 g of dichloromethane was placed. Then, 0.1 g (0.001 mol) of sulfuric acid was added to and mixed well by shaking with the dichloromethane. The resulting solution was left still. It was found that some amount of the sulfuric acid was adhered to an inner surface of the glass container without being dissolved in the dichloromethane. This 5-g dichloromethane solution of the sulfuric acid was provided as an acid catalyst solution. In a 10-mL lidded polyethylene container, 9 g (0.3 mol in terms of formaldehyde) of trioxane was placed. While externally cooling the container with ice, 30 g (1.5 mol) of hydrogen fluoride was added into the container. The lid of the container was closed. The trioxane was then dissolved in the hydrogen fluoride. The lid of the container was opened after confirming that the content of the container was in the form of a uniform solution. Subsequently, 20 g of dichloromethane was added to the uniform solution. The lid of the container was closed. The resulting solution was mixed well by shaking, left still and thereby separated into a lower dichloromethane layer and an upper hydrogen fluoride layer. The lower dichloromethane layer was isolated. To the upper hydrogen fluoride layer, 20 g of dichloromethane was again added. The lid of the container was closed. The resulting solution was then mixed well by shaking and left still. The lower dichloromethane layer was isolated and blended with the previously isolated dichloromethane layer. The same operation was repeated again. With this, about 53 g of the transparent dichloromethane solution was obtained. Some amount of the obtained dichloromethane solution was sampled. The hydrogen fluoride dissolved in the sampled dichloromethane solution was fixed with sodium fluoride powder. After that, the dichloromethane solution was analyzed by gas chromatography. There was detected 0.03 mol of bisfluoromethyl ether in the dichloromethane solution. Into this dichloromethane solution, 6 g (0.036 mol) of hexafluoroisopropyl alcohol was added and mixed. Immediately after the mixing, some amount of the mixed dichloromethane solution was sampled. The hydrogen fluoride dissolved in the sampled dichloromethane solution was fixed with sodium fluoride powder. The dichloromethane solution was then analyzed by gas chromatography. There was newly detected 0.036 mol of HFIP in addition to the 0.03 mol of bisfluoromethyl ether (FE) in the dichloromethane solution. The generation of fluoromethyl hexafluoroisopropyl ether (SEVO) was not however detected at all. Next, 10 g of this FE- and HFIP-containing dichloromethane solution was placed in a 100-mL polyethylene container and mixed with the above-prepared 5-g dichloromethane solution of the sulfuric acid. At the time the resulting mixed solution was held at 25° C. for 15 hours, the reaction was completed. After the completion of the reaction, while externally cooling with ice the polyethylene container accommodating therein the mixed solution, the lid of the polyethylene container was opened. Ice was then added into the mixed solution. The lid of the polyethylene container was closed. The mixed solution was mixed well by shaking, thereby terminating the reaction. The reaction-terminated solution was left still. The thus-formed lower dichloromethane layer was isolated, dried with sodium sulfate, and then, analyzed by gas chromatography. As a result, the generation of SEVO was confirmed. The yield of the SEVO on the FE basis was 38% as determined from the ratio of peak areas in the gas chromatograph.

Example 2

The experiment was conducted in the same manner as in Example 1 except for using trifluoromethanesulfonic acid as an acid catalyst. The acid catalyst was prepared as follows. In a 20-mL lidded glass container, 5 g of dichloromethane was placed. Then, 0.15 g (0.001 mol) of trifluoromethanesulfonic acid was added to and mixed well by shaking with the dichloromethane. The resulting solution was left still. It was found that some amount of the trifluoromethanesulfonic acid remained separated on a bottom of the glass container without being dissolved in the dichloromethane. This 5-g dichloromethane solution of the trifluoromethanesulfonic acid was provided as an acid catalyst solution. In a 100-mL lidded polyethylene container, 10 g of the FE- and HFIP-containing dichloromethane solution as obtained in Example 1 was placed and mixed with the prepared 5-g dichloromethane solution of the trifluoromethanesulfonic acid (acid catalyst solution). At the time the resulting mixed solution was held at 25° C. for 15 hours, the reaction was completed. After the completion of the reaction, while externally cooling with ice the polyethylene container accommodating therein the mixed solution, the lid of the polyethylene container was opened. Ice was then added into the mixed solution. The lid of the polyethylene container was closed. The mixed solution was mixed well by shaking, thereby terminating the reaction. The reaction-terminated solution was left still. The thus-formed lower dichloromethane layer was isolated, dried with sodium sulfate, and then, analyzed by gas chromatography. The generation of SEVO was confirmed. The yield of the SEVO on the FE basis was 58% as determined from the ratio of peak areas in the gas chromatograph.

Comparative Example 1

The experiment was conducted in the same manner as in Example 1 except for using methanesulfonic acid (pKa=−1.2) as an acid catalyst as follows. Into 5 g of dichloromethane, 0.1 g (0.001 mol) of methanesulfonic acid was added and mixed well by shaking. The resulting solution was left still. It was confirmed that the methanesulfonic acid was dissolved in the dichloromethane. This 5-g dichloromethane solution of the methanesulfonic acid was provided as an acid catalyst solution. In a 100-mL lidded polyethylene container, 10 g of the FE- and HFIP-containing dichloromethane solution as obtained in Example 1 was placed and mixed with the prepared 5-g dichloromethane solution of the methanesulfonic acid (acid catalyst solution). At the time the resulting mixed solution was held at 25° C. for 15 hours, the reaction was completed. After the completion of the reaction, while externally cooling with ice the polyethylene container accommodating therein the mixed solution, the lid of the polyethylene container was opened. Ice was then added into the mixed solution. The lid of the polyethylene container was closed. The mixed solution was mixed well by shaking, thereby terminating the reaction. The reaction-terminated solution was left still. The thus-formed lower dichloromethane layer was isolated, dried with sodium sulfate, and then, analyzed by gas chromatography. The generation of SEVO was not almost detected.

Comparative Example 2

The experiment was conducted in the same manner as in Example 1 except for using paratoluenesulfonic acid (pKa=−2.8) as an acid catalyst as follows. In a 20-mL lidded glass container, 5 g of dichloromethane was placed. Then, 0.17 g (0.001 mol) of paratoluenesulfonic acid was added to and mixed well by shaking with the dichloromethane. The resulting solution was left still. It was confirmed that the paratoluenesulfonic acid remained separated as a solid on a bottom of the glass container without being dissolved in the dichloromethane. This 5-g dichloromethane solution of the paratoluenesulfonic acid was provided as an acid catalyst solution. In a 100-mL lidded polyethylene container, 10 g of the FE- and HFIP-containing dichloromethane solution as obtained in Example 1 was placed and mixed with the prepared 5-g dichloromethane solution of the paratoluenesulfonic acid (including the undissolved paratoluenesulfonic acid). At the time the resulting mixed solution was held at 25° C. for 15 hours, the reaction was completed. After the completion of the reaction, while externally cooling with ice the polyethylene container accommodating therein the mixed solution, the lid of the polyethylene container was opened. Ice was then added into the mixed solution. The lid of the polyethylene container was closed. The mixed solution was mixed well by shaking, thereby terminating the reaction. The reaction-terminated solution was left still. The thus-formed lower dichloromethane layer was isolated, dried with sodium sulfate, and then, analyzed by gas chromatography. The generation of SEVO was not almost detected.

As described above, it is possible according to the present invention to enable industrial production of the fluoromethyl hexafluoroisopropyl ether (($CF_3$)$_2$CH—O—$CH_2$F) without using hydrogen fluoride or a large amount of sulfuric acid as an acid and thereby without causing a large amount of acid waste as a by-product.

Although the present invention has been described with reference to the above specific embodiments, the present invention is not limited to these exemplary embodiments. Various modifications and variations of the embodiments described above can be made without departing from the scope of the present invention.

The invention claimed is:

1. A process for producing fluoromethyl hexafluoroisopropyl ether, comprising: reacting bisfluoromethyl ether with hexafluoroisopropyl alcohol in a solvent of dichloromethane in the presence of a catalytic amount of a strong acid selected from sulfuric acid and any other acids stronger in acidity than sulfuric acid, wherein the amount of the strong acid used is 0.0001 to 10 parts by mass per 100 parts by mass of a reaction solution.

2. The process for producing fluoromethyl hexafluoroisopropyl ether according to claim 1, wherein the strong acid is one kind, or two or more kinds, selected from sulfuric acid, trifluoromethanesulfonic acid and fluorosulfuric acid.

3. The process for producing fluoromethyl hexafluoroisopropyl ether according to claim 1, wherein the reacting is performed at 0 to 150° C.

* * * * *